US010156529B2

(12) United States Patent
Nakayama et al.

(10) Patent No.: US 10,156,529 B2
(45) Date of Patent: Dec. 18, 2018

(54) METHOD FOR DISPLAYING/ANALYZING BODY FLUID ABSORPTION MODE OF ABSORBENT ARTICLE

(71) Applicants: DAIO PAPER CORPORATION, Ehime (JP); NATIONAL UNIVERSITY CORPORATION TOTTORI UNIVERSITY, Tottori (JP)

(72) Inventors: Bin Nakayama, Tottori (JP); Yoshiko Suyama, Tottori (JP); Kaori Fujii, Tottori (JP); Junichi Kishimoto, Tottori (JP); Toshio Sakou, Tottori (JP); Aya Ohshima, Tochigi (JP)

(73) Assignees: DAIO PAPER CORPORATION, Ehime (JP); NATIONAL UNIVEERSITY CORPORATION TOTTORI UNIVERSITY, Tottori (JP)

(*) Notice: Subject to any disclaimer, the term of this patent is extended or adjusted under 35 U.S.C. 154(b) by 189 days.

(21) Appl. No.: 15/108,489

(22) PCT Filed: Dec. 26, 2014

(86) PCT No.: PCT/JP2014/084451
§ 371 (c)(1),
(2) Date: Jun. 27, 2016

(87) PCT Pub. No.: WO2015/099104
PCT Pub. Date: Jul. 2, 2015

(65) Prior Publication Data
US 2016/0327496 A1    Nov. 10, 2016

(30) Foreign Application Priority Data

Dec. 27, 2013   (JP) .................................. 2013-272253

(51) Int. Cl.
G01N 23/04         (2018.01)
A61F 13/84         (2006.01)
G01N 23/046        (2018.01)

(52) U.S. Cl.
CPC ........... *G01N 23/046* (2013.01); *A61F 13/84* (2013.01); *A61F 2013/8488* (2013.01); *A61F 2013/8491* (2013.01)

(58) Field of Classification Search
CPC ...... A61F 2013/8491; A61F 2013/8488; A61F 13/84; G01N 23/046
See application file for complete search history.

(56) References Cited

U.S. PATENT DOCUMENTS

2004/0066879 A1* 4/2004 Machida ................ A61B 6/027
378/4
2008/0034849 A1* 2/2008 Honkonen ........ A61F 13/15203
73/73

(Continued)

FOREIGN PATENT DOCUMENTS

JP      2010-074031 A     4/2010
JP      2011-212043 A     10/2011

(Continued)

OTHER PUBLICATIONS

Heindel et al., "An X-ray system for visualizing fluid flows," ScienceDirect, Flow Measurement and Instrumentation 19 (2008) pp. 67-78.

*Primary Examiner* — Glen Kao
(74) *Attorney, Agent, or Firm* — Muncy, Geissler, Olds & Lowe, P.C.

(57) ABSTRACT

To know an absorption and diffusion state with time of drainage. In a state in which an absorbent article is put on a human body type dummy doll equipped with a body fluid-supplying means, the absorbent article is photographed after the fluid is excreted from the dummy doll by an X-ray CT (Continued)

apparatus; and at least one absorption modes of absorption modes of the drainage into the absorbent article after the excretion in the state in which the absorbent article is put on the dummy doll, and absorption dynamics of the drainage on the absorbent article after the excretion is displayed/analyzed based on the photographed image.

7 Claims, 7 Drawing Sheets

(56) References Cited

U.S. PATENT DOCUMENTS

| | | | |
|---|---|---|---|
| 2011/0243425 A1 | 10/2011 | Maltbie et al. | |
| 2011/0245651 A1* | 10/2011 | Nakamura | A61B 5/055 600/407 |
| 2011/0249795 A1 | 10/2011 | Sugita et al. | |
| 2012/0321040 A1* | 12/2012 | Maltbie | G01N 23/04 378/62 |

FOREIGN PATENT DOCUMENTS

| | | |
|---|---|---|
| JP | 5058526 B2 | 10/2012 |
| WO | WO 2010/074031 A1 | 7/2010 |

* cited by examiner

<Front of ventral side>
(Improved product)

Reduced amount of urine excreted on ventral side

METHOD FOR DISPLAYING/ANALYZING BODY FLUID ABSORPTION MODE OF ABSORBENT ARTICLE

TECHNICAL FIELD

The present invention relates to a method for displaying/analyzing a body fluid absorption mode of an absorbent article.

BACKGROUND ART

In developing or improving absorbent articles such as a disposable diaper, a sanitary napkin, and absorbent pad, it is very important to know how drainage of body fluid such as urine or menstrual blood is absorbed in the absorbent articles.

For this end, there is a method for analyzing a body fluid absorption mode in an absorbent article by collecting actually used absorbent articles in which body fluid is excreted and visually observing an absorption and diffusion state of the drainage.

According to that method, however, not only much labor and time are necessary for testing and recovering the absorbent articles but also feedback to development cannot be carried out smoothly.

According to the analysis system to know this situation, although typical results of drainage can be obtained, it cannot be expected to obtain extreme results of drainage, and thus it is impossible to feedback results including the extreme results of drainage to the development.

It is also impossible to evaluate an influence by change of a drainage amount on the absorption and diffusion state of the drainage.

It is further impossible to evaluate an influence by change of a posture during excretion on the absorption and diffusion state of the drainage.

Furthermore, it is actually impossible to understand change with time of a leakage state of drainage.

There is a method for analyzing a body fluid absorption mode of an absorbent article using a dummy doll for excretion, which is a human body type dummy doll having an absorbent article to which a body fluid-supplying means is added.

This is a method in which using a dummy for excretion having a shape similar to the torso and upper extremity of a human body and formed of a flexible material such as silicone rubber (which further includes dummy dolls capable of deforming their positions of the body such as a dummy doll for excretion capable of changing an angle between the torso and the upper extremity, and a dummy doll capable of alternatively swinging legs in relation to the torso like walking back and forth), for example, artificial urine or artificial menstrual blood is injected into a drainage path in the dummy doll for excretion, and absorption results finally obtained from drainage from private parts for excretion of human to absorbent article are analyzed as a body fluid absorption mode of the absorbent article.

Various kinds of the dummy dolls described above are known. (Examples are described in Patent Document 1).

CITATION LIST

Patent Documents

Patent Document 1: Japanese Patent No. 5058526

SUMMARY OF INVENTION

Technical Problem

According to a mainly used conventional method for analyzing the body fluid absorption mode of the absorbent article, however, the absorbent article is removed from the dummy for excretion after completion of the excretion, and then the drainage state of the used surface side is evaluated in a developed state of the article.

It is impossible, accordingly, to know basically an absorption and diffusion situation of the drainage with time, and the leakage cannot be accurately obtained as well. With respect to the latter, it is absolutely impossible to know a starting point of the leakage, and the presence or absence of the leakage cannot be found until the drainage is actually leaked from the outside of a product.

Further, it is also impossible to understand the relationship between an amount of drainage injected and an absorption and diffusion situation with time.

A main object of the present invention is to provide a method for displaying/analyzing a body fluid absorption mode of an absorbent article from which an absorption and diffusion situation with time of drainage can be known.

Solution to Problem

The present inventions which have solved the problems described above are as follows:

Previously, the definition of the term "display/analyze" in the present invention is clarified. The term "display/analyze" in the present invention has meanings including (1) a condition in which a body fluid absorption mode of an absorbent article is displayed on a displaying means; (2) a condition in which the body fluid absorption mode of the absorbent article is not displayed on the displaying means but can be perceived by a person who makes final decision, for example, the body fluid absorption mode itself is not output but results of the analysis or evaluation of the absorption mode are output; (3) a condition in which the body fluid absorption mode of the absorbent article is displayed on the displaying means and, at the same time, the results of analysis or evaluation of the absorption mode can be perceived by a person who makes final decision, and the like.

The term "body fluid" has a meaning including urine and menstrual blood excreted from a human body, including artificial urine and artificial menstrual blood, in addition to human excrement. The artificial body fluid further includes fluid to which a developer is added for improving an image. A physiological saline solution, and the like to which a developer is added is also included. The term "drainage" refers to liquid which is in particular excreted or drained from, a dummy doll, among the body fluid described above.

A method for displaying/analyzing a body fluid absorption mode of an absorbent article comprising the steps of in a state in which an absorbent article is put on a human body type dummy doll equipped with a body fluid-supplying means, photographing the absorbent article after the fluid is excreted from the dummy doll by an X-ray CT apparatus; and displaying/analyzing, based on the photographed image, at least one absorption dynamics of absorption modes of the drainage into the absorbent article after the excretion in the state in which the absorbent article is put on the dummy doll, and absorption modes of the drainage on the absorbent article.

<Effects>

In order to know the absorption and diffusion state with time of the drainage (such as urine or menstrual blood) in the absorbent article, the X-ray CT apparatus is used. The human body type dummy doll equipped with the body fluid-supplying means is also used. In the state in which the absorbent article is put on the dummy doll, the absorbent article is photographed by the X-ray CT apparatus after the drainage is excreted from the dummy doll (of course, it is possible to start the photographing before the excretion and this mode is naturally included).

As a result, the absorption mode of the drainage into the absorbent article after the excretion, and the change with time of the absorption mode, i.e., an "absorption dynamics" of the drainage on the absorbent article can be known.

In addition to the display of the photographed image as it is, it is possible to reconstruct the photographed image into a three-dimensional image or moving image (animation) so that an observer or analyzer can easily understand it; to make a colored image not a monochrome image; to extract only attention parts (other parts to be distinguished are deleted as much as possible); to color the attention parts; or to display a three dimensional image, which has been subjected to a viewpoint conversion, by a displaying means such as a monitor screen or a reproduction screen of a recording apparatus.

The method of the invention may also include an analyzing operation, for example, once information (raw data information or reconstructed information) is recorded in a recording apparatus, and then the information is displayed/analyzed, or information is processed and it is subjected to various analysis processing, and the like into, for example, emphasized information. The analysis in the present invention includes both of analyses performed by observers and analyses performed by an information processing apparatus.

According to the present invention, the absorption and diffusion state with time of the drainage can be basically known. The starting site and the starting time point of the leakage can also be understood.

Furthermore, according to the conventional analysis of the absorption mode of the body fluid (drainage) on the absorbent article, it is main stream that the absorbent article is removed from a dummy doll for excretion after the excretion is completed and then the drainage state is evaluated in a developed state of the absorbent article on the used side. On the other hand, according to the present invention, it is possible to know the absorption and diffusion mode in a state in which the absorbent article is put on the doll without development of the absorbent article, and it is possible to make very accurate judgement.

As the image photographed by the X-ray CT apparatus is not an image of a human body on which an absorbent article is put but the dummy doll, it hardly raises the problem of exposure to X-rays. It is also possible to photograph the doll taking various body positions and thus an amount of information available becomes huge.

In any case, it is considered to be the beginning and a foothold for considerable progress of the quality improvement and development of the absorbent article that the change with time of the absorption and diffusion state of the drainage can be understood.

The method for displaying/analyzing a body fluid absorption mode of an absorbent article, wherein the human body type dummy doll equipped with the body fluid-supplying means is configured so as to pass a sample liquid through the inside of the human body type dummy doll and to drain the liquid from private parts imitating the human body by the body fluid-supplying means.

<Effects>

When the dummy doll is configured so that the sample liquid is passed through the human body type dummy doll by the body fluid-supplying means and is drained from the private part imitating the human body, a correlation with actual excretion by a human body is high, and thus an accurate absorption and diffusion state of the drainage can be understood.

The method for displaying/analyzing a body fluid absorption mode of an absorbent article, wherein the absorbent article is a disposable diaper having a CT value of −940 HU to −920 HU.

<Effects>

A main material of diapers is polyethylene, a non-woven fabric, cotton-like pulp, crepe paper, or the like. The diaper has a CT value of about −940 HU to −920 HU.

On the other hand, in terms of the flexibility, formability, and the like, silicone rubber, urethane, or the like as a material is used for the dummy doll, which has a CT value of about −60 HU to −45 HU (−52 HU in average). The artificial urine has a CT value of about 5 HU to 40 HU (20 HU in average).

The air has a CT value of −1000 HU, which is close to the CT value of the diaper, and thus it is very difficult to draw the diaper.

The present inventors have found that it is possible to draw the diaper by performing the information processing and further the image processing of the photographed image information, and with respect to the drainage (artificial urine) on the diaper, it is possible to display the distinguished state of absorption and diffusion of the drainage (artificial urine) because of the different CT value.

The method for displaying/analyzing a body fluid absorption mode of an absorbent article, wherein the X-ray CT apparatus has a helical scan photographing means and a multi-row detector of X-rays.

<Effects>

When the X-ray CT apparatus has the helical scan photographing means and the multi-row detector of X-rays, detail information can be obtained, an image can be easily processed into a three-dimensional image, and target parts can be displayed in detail.

The method for displaying/analyzing a body fluid absorption mode of an absorbent article, wherein the photographed CT image is subjected to a reconstruction image processing to reconstruct a three-dimensional image, and the processed image is displayed on a displaying means.

<Effects>

When the photographed CT image is subjected to the reconstruction image processing to reconstruct the three-dimensional image, and the processed image is displayed on the displaying means, the image can be easily perceived and the judgement and analysis can be made precise.

The method for displaying/analyzing a body fluid absorption mode of an absorbent article, wherein the CT images of the drainage state with time are subjected to a reconstruction image processing to reconstruct a three-dimensional image, and the processed images changed with time are displayed as a moving image on a displaying means.

<Effects>

When the image is subjected to the reconstruction image processing to reconstruct the three-dimensional image and the obtained images changed with time are displayed on the displaying means as a moving image, the change with time of the absorption and diffusion state can be more clearly understood.

The method for displaying/analyzing a body fluid absorption mode of an absorbent article, wherein a body position of the human body type dummy doll equipped with the body fluid-supplying means is changed, and a change of an absorption mode of urine by the change of the body position is displayed/analyzed.

<Effects>

Conventionally, with respect to knowing about the change of the absorption mode of urine accompanying the change of the body position, it is limited to only the judgement that a leakage can be more easily caused when a specific position is taken. On the other hand, according to the present invention, when the body position of the human body type dummy doll is changed and is displayed/analyzed, the change of the absorption mode of the urine can be known in many kinds of the body positions because the body position of the human body type dummy doll can be easily changed, and thus the analysis can be accurately performed.

The method for displaying/analyzing a body fluid absorption mode, which comprises the steps of; previously knowing a relationship between a shape of a known dummy doll and a shape of a known absorbent article put on the doll; applying a shape of the absorbent article photographed to the dummy doll in the photographed image; understanding a relationship between the absorbent article and the photographed drainage; and understanding an absorption mode of the drainage in the absorbent article.

<Effects>

As described above, the air has a CT value of −1000 HU, which is close to the CT values of a diaper or a sanitary napkin using the same kind of material. For that reason, it is extremely difficult to draw the diaper or sanitary napkin. The present inventors, however, have found that it is possible to draw the diaper by performing information processing, and further image processing, of the information photographed.

However, this requires much labor. When a simplified method thereof has been explored, it has been found that a recent CAD technique can be applied.

The relationship (Relationship 1) between the shape of the known dummy doll and the shape of the known absorbent article when the doll puts on the known absorbent article can be previously easily known as three-dimensional information (CAD) through photographing, or the like. Then, the shape of the absorbent article photographed is applied to the dummy doll in the photographed image based on Relationship 1; the relationship (Relationship 2) between the absorbent article and the drainage photographed is understood; and the shape of the drainage, and the like on the absorbent article is understood on the image or the CAD screen, whereby the absorption mode of the body fluid can be understood.

Advantageous Effects of Invention

According to the present invention, it is possible to display/analyze the body fluid absorption mode of the absorbent article from which the absorption and diffusion mode with time of the drainage can be known.

DESCRIPTION OF EMBODIMENTS

Figure 1:
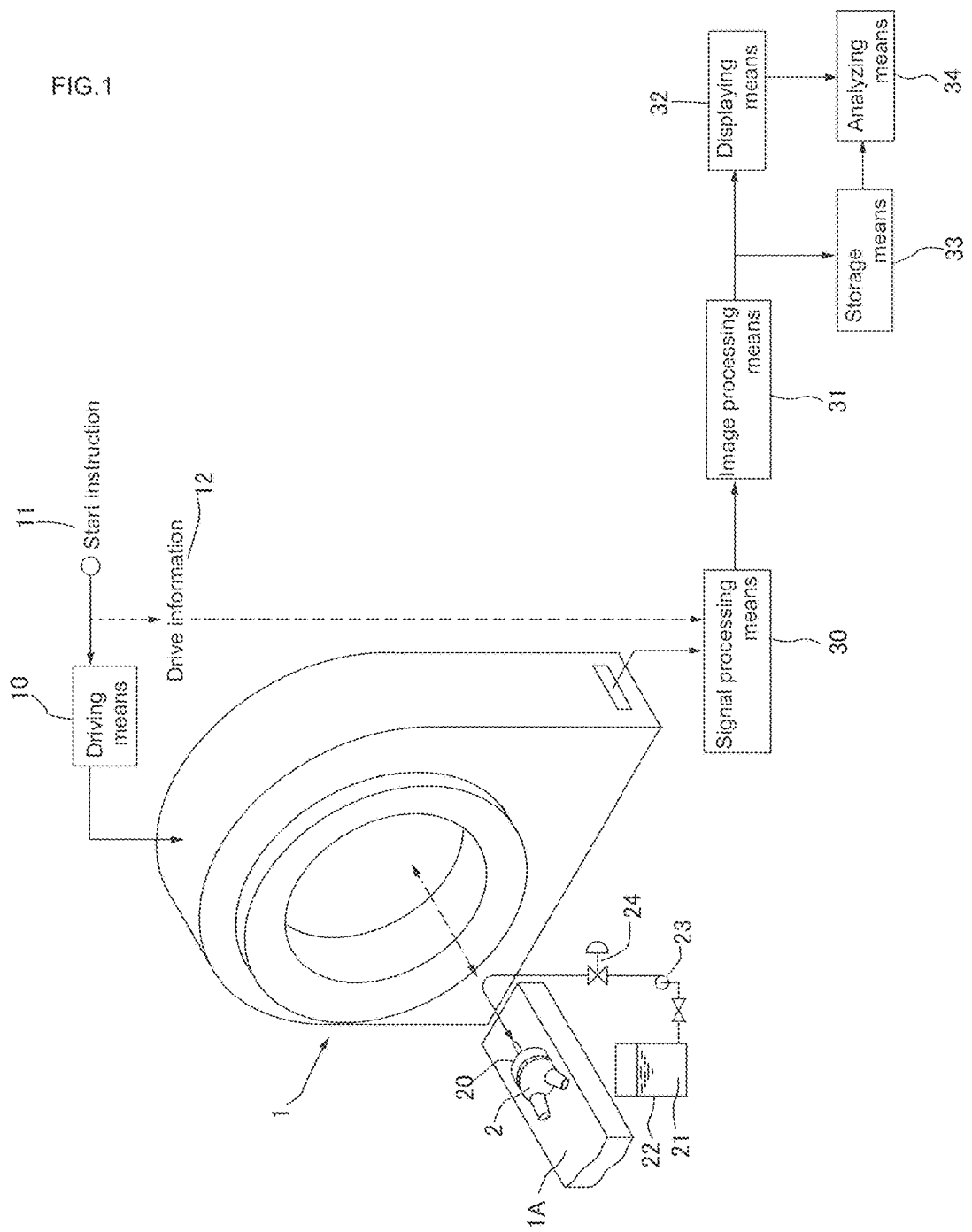
FIG. 1 is an outline explanation view of a construction of an apparatus for carrying out the present invention.

Referring to the drawings attached, embodiments of the present invention are explained in detail below.

An X-ray CT (Computed Tomography) apparatus 1 is an apparatus in which a test object is put between an X-ray source and a detector, and signals resulting from attenuations of X-rays by the test object put are converted into an image.

The X-ray CT apparatus 1 illustrated in the drawing contains an X-ray source and a detector (not shown) therein. The X-ray source and the detector turn around the test object, which is a detection object; the test object receives X-rays from every direction; the applied X-rays pass through the test object, are attenuated by absorption of a part thereof into the object, and then reach an X-ray detector located at an opposite side of the X-ray source; and the obtained data are recorded. After a degree of the absorption is recorded in each direction, an image is reconstructed by performing a Fourier transform with a computer.

On the reconstruction, one cross-section is divided a lattice pattern into, an absorption rate of each part is defined as an unknown number, simultaneous equations are made so that the total thereof is equal to an actual absorption amount, and the simultaneous equations are solved.

The X-ray CT apparatus 1 is provided with a rotary driving means 10 for the X-ray source and the detector, and start information 11 is provided thereto and drive information 12 such as driving timing is provided to an image processing system described below.

A test object of a human body type dummy doll 20 equipped with a body fluid-supplying means on which an absorbent article 2 is put is set on a bed 1A. The example illustrated shows a state in which a disposable diaper is put on the dummy doll 20, and the doll is set in a state of laying on its back.

The dummy doll 20 contains the body fluid-supplying means. The body fluid-supplying means is constituted so that artificial urine, which is sample liquid, is passed from a reservoir 22 for artificial urine 21 through a path formed in the dummy doll 20 by a pump 23 and is drained from a private part (urination opening, not shown) imitating the human body. Information including the supply and injection amount of the drainage, supplying timing, and accumulated supply amount is provided as basic information to an analyzing means 34 described below, and the like. 24 shows a flow rate controlling valve.

A preferable X-ray CT apparatus 1 in the present invention is a helical scan type, which has an X-ray multi-row detector.

As the helical scan, a single helical scan photographing means may be used, but a multi-helical scan type is preferable.

The image signal information from the X-ray source and detector in the X-ray CT apparatus 1 is appropriately processed and analyzed according to the objective for detection and the analysis item.

The example above is explained below.

For example, raw data (digital data) from the detector obtained by projection is converted into digital signals through a signal processing means 30, and an image is reconstructed therefrom. Upon the reconstruction of the image, for example, a convolution backprojection (CBP) method can be used. According to the CBP method, convolution and backprojection are performed.

An "image reconstructing function" which performs the convolution is changed by row data, whereby images having various spatial resolutions and contrast resolutions can be constructed. If there are raw data obtained by the helical scan, it is also possible to reconstruct them by changing an image reconstruction interval.

As the image reconstruction method, a "successive approximation method" is useful, and in particular, an ASiR method available from General Electric Company (an application method of the successive approximation method, which is a method for deleting noise components by successively recalculating statistical noise patterns without deterioration of spatial resolution, which is a "Veo" method) is also extremely useful.

That method is a successive approximation reconstruction method considering geometric information of X-ray in the CT apparatus itself including a focal point size, a detector cell size, a reconstruction pixel size, and X-ray fluxes passing therethrough, and fluctuation of X-ray photons. According to the method, physical phenomena occurring upon the photographing, for example, a position of a patient, a size of a focal point of X-ray, a cell size of X-ray detector, an image voxel size, and geometric shadows of X-rays connecting the above items, which have been excluded in a conventional CT, are mathematically subjected to modeling, which are incorporated into a calculation process in the successive approximation reconstruction, to which various noise models are added, and detailed reconstruction is performed.

As a specific unit of CT, there is a CT value. The CT value is represented by the following formula and shows a degree of an X-ray absorption of an object. In a CT apparatus, an absorption coefficient is defined as 0 when water is scanned.

$$\text{CT value} = (\mu t - \mu w)/\mu w \times 1000 \qquad (1)$$

In the formula, $\mu t$ is an X-ray absorption coefficient of the object, and $\mu w$ is an X-ray absorption coefficient of water. The air has a CT value of −1,000.

In the CT apparatus, even if an X-ray dose (a tube voltage, a tube current, and a scanning time) is changed, the CT value is not changed.

As a material for the dummy doll, silicone rubber, urethane, or the like is used in terms of the flexibility, formability, and the like, and the CT value thereof is from about −60 HU to −45 HU (−52 HU in average). The artificial urine has a CT value of about 5 HU to 40 HU (20 HU in average). The diaper has a CT value of about −940 HU to −920 HU, which is close to the CT value of the air, −1000 HU. As a result, it is very difficult to draw the diaper.

For those reason, it is preferable to utilize a "window function" (a function for partly luminance displaying CT value information of a CT image) when an image is displayed on a displaying means 32, and a concentration and a contrast of the image are controlled, i.e., a minute CT value difference is expressed with a sufficient contrast by selecting only the desired CT value range, and displaying the width thereof with 256 gradation.

A window width is a CT value range selected and a window level is a median value in the CT value range selected in the "window function," and they are appropriately selected.

When the window width or window level is changed, a CT image displayed is changed, and shade of the CT image is generally changed by operating the window level. When the window level is raised, an image density becomes black, and when the window level is reduced, the image density becomes white. When the window width is widened, visual noises of the image is decreased, but the minute CT value difference cannot be expressed with a sufficient contrast. On the contrary, when the window width is narrowed, the visual noise of the image is increased, but the minute CT value difference can be expressed with a sufficient contrast.

It is desirable to three-dimensionally display the reconstructed image data in an image processing means 31 by a three-dimensional display technique. As the three-dimensional display technique, multi planar reconstruction (MPR), maximum intensity projection (MIP), or the like can be used in addition to surface rendering and volume rendering.

It is desirable to convert the three-dimensional display data into moving image (animation) data. It is also possible to display the three-dimensional display data or the moving image (animation) data as it is on the displaying means 32 such as a CRT displaying apparatus, and it is also possible that the data is once stored in a storage unit 33, the storage data is taken out when needed, and an analyzing processing thereof is performed in the analyzing means 34 for the evaluation of the absorbent article, and the like.

Concrete examples in which the X-ray CT apparatus 1 is utilized for the evaluation of the disposable diaper 2, and the like are explained.

First, an absorbent article 2 to be evaluated is put on the human body type dummy doll 20, and, in the drawing illustrated, the doll, taking a pre-determined posture, is set in a state of laying on its back on the bed 1A. At that time, it is preferable to previously put a liquid-nonpermeable sheet for inhibiting staining on the bed 1A beforehand.

A body fluid-supplying means is connected to the dummy doll 20. Subsequently, the bed 1A is transported, and the dummy doll 20 is put into a projection position.

While such a state is maintained, a start command 11 is provided to the driving means 10 to start the photographing. A pump 23 is also started, and artificial urine 21 is sent from the reservoir 22 to an injection path in the dummy doll 20 at a pre-determined injection rate per unit time and is drained from an urination opening of the dummy doll 20. The artificial urine drained is absorbed in the disposable diaper 2 and diffused with time.

The signal processing described above is performed, which the CT information is fetched for the whole process of the absorption and diffusion of the artificial urine for all time.

Figure 2:
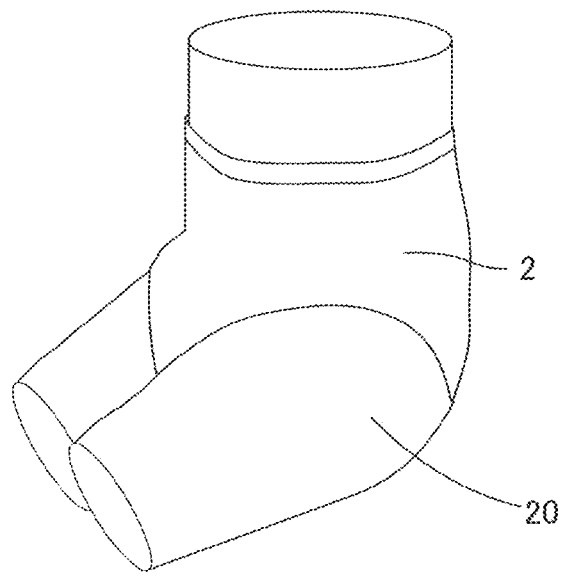
FIG. 2 is an oblique view showing an example of a dummy doll with a different body position in a sitting state.
Figure 3:
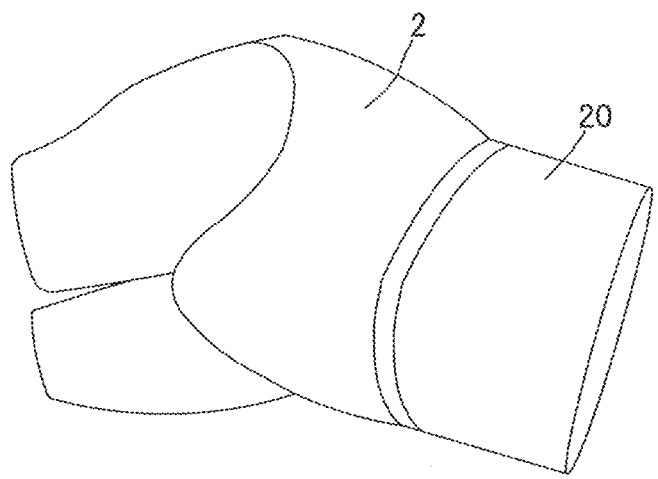
FIG. 3 is an oblique view showing an example of a dummy doll with a different body position in a horizontal state.

It is further possible that the posture of the dummy doll 20 is changed to a sitting position similar to a state in which a person sits in a chair as shown in FIG. 2, to a lateral state as shown in FIG. 3, or the like, and the same test as above is performed. If necessary, the same test as above can also be performed in a state in which the legs of the dummy doll 20 are crossed and tied with string, and the like.

Another test item includes a leakage rate of the artificial urine, which controls the flow rate controlling valve 24. The test can also be performed changing a size or body shape of the dummy doll 20.

As the dummy doll, in addition to a part of the body thereof, a whole body dummy may be used. As shown in Patent Document 1, a dummy in which a separate torso and separate legs are connected to each other may be used.

The present invention can also be naturally applied to the display/analysis of the body fluid absorption mode in sanitary napkins. In the case of the sanitary napkin, a test can be performed in a manner in which the sanitary napkin is put on the dummy doll and shorts are put thereon, which is subjected to the X-ray CT apparatus 1. In this case, it is possible to use artificial menstrual blood or proper liquid imitating the menstrual blood.

Example 1

As the X-ray CT apparatus, a multi-slice helical apparatus (a model "Discovery CT750 HD") having 64 rows of detectors, manufactured by General Electric Company, was used.

An experiment was performed in an outline construction as shown in FIG. 1. The posture of the dummy doll was not a posture shown in FIG. 1 but a lateral decubitus inclined in the lower-left by 20°. With respect to each disposable diaper, CT images were obtained during an injection process in which an artificial urine amount per time was 150 ml and an injection rate was 10 ml/second, and the analysis thereof was performed.

The artificial urine used herein contained a component composition of 20% of urea, 8% of sodium chloride, 0.30% of calcium chloride, 0.80% of magnesium sulfate, 70.90% of ion exchanged water, and a slight amount of coloring matter, which had a CT value of 20 HU.

CT images were observed on the monitor, and three-dimensional images and animation images (four-dimensional images) thereof were submitted to observers for their decision.

Figure 4:
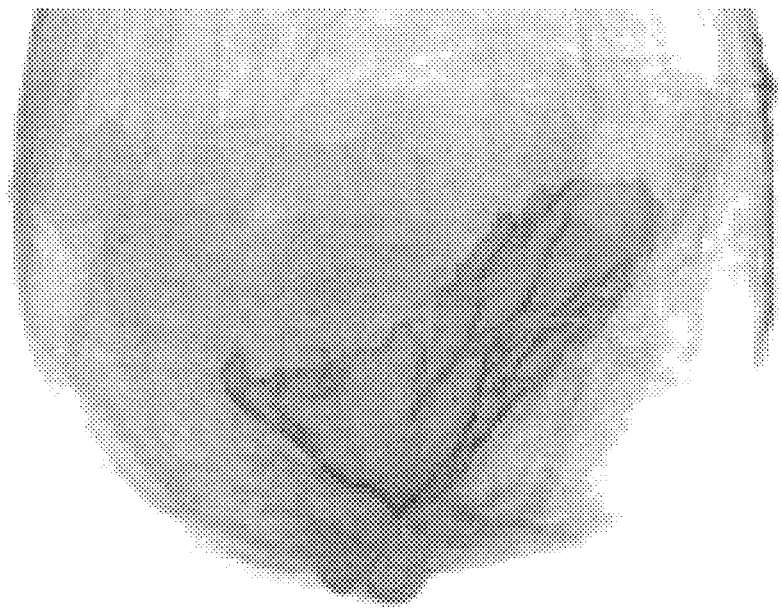
FIG. 4 is a view showing a three-dimensional display result of an absorption and diffusion state of drainage in an existing product.
Figure 6:
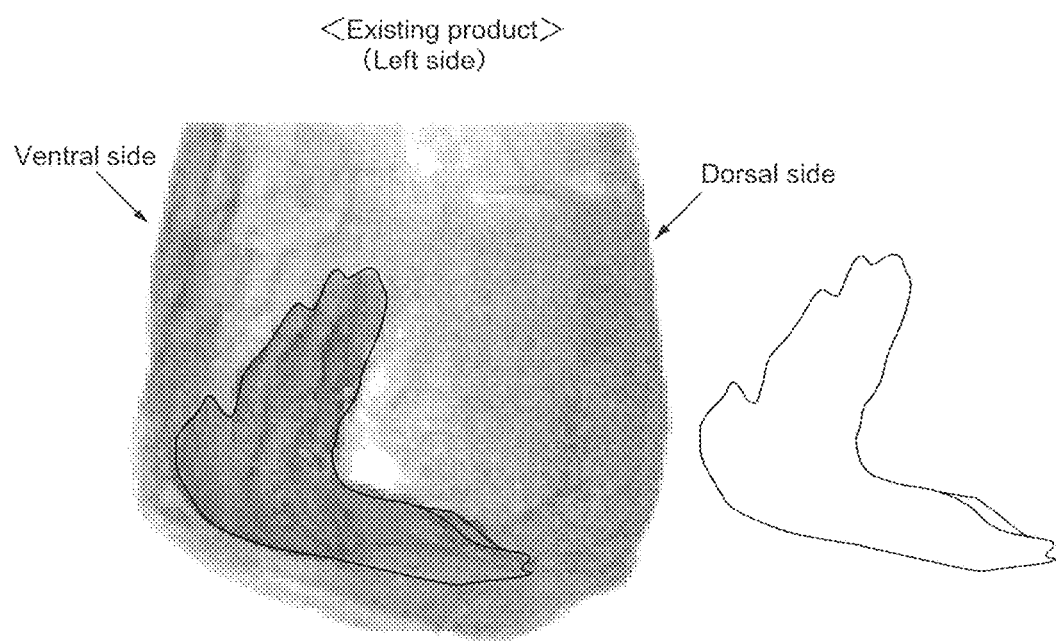
FIG. 6 is a view showing a three-dimensional display result of an absorption and diffusion state of drainage in an existing product from a different viewpoint.
Figure 7:
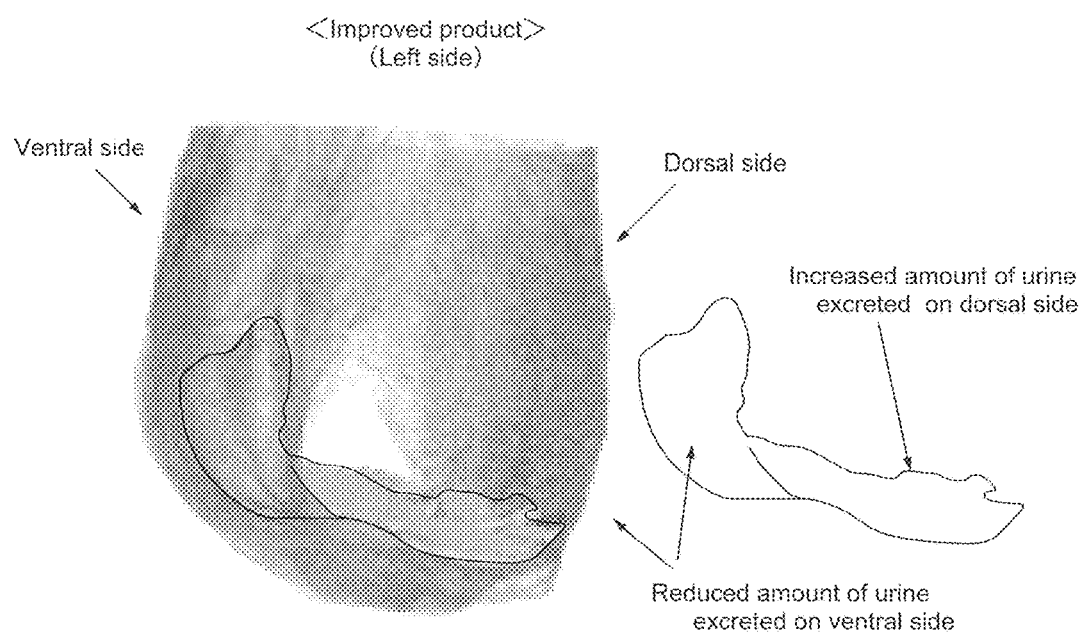
FIG. 7 is a view showing a three-dimensional display result of an absorption and diffusion state of drainage in an improved product from a different viewpoint.

As a result, it was proved that, in the case of the existing products, the diffusion of the urine excreted on a ventral side was large, thus resulting in a high probability of occurrence of the leakage, as shown in FIG. 4 and FIG. 6.

Figure 5:
FIG. 5 is a view showing a three-dimensional display result of an absorption and diffusion state of drainage in an improved product.

The same experiment as above was performed except that the construction of the product was improved. As a result, in the case of the improved product, the diffusion of the urine excreted on the ventral side was reduced and, on the contrary, the diffusion amount on the dorsal side was large, as shown in FIG. 5 and FIG. 76. It was proved, however, that the possibility of the occurrence of leakage was remarkably reduced because of the reduced diffusion of the urine excreted on the ventral side.

Example 2

The experiment of a sanitary napkin was performed in an outline construction as shown in FIG. 1.

CT images were obtained during an injection process of 30 ml of an artificial menstrual blood amount per time and an injection rate of 1 ml/second, and the analysis thereof was performed.

The artificial menstrual blood used herein contained a component composition of glycerol, sodium carboxymethyl cellulose, sodium chloride, sodium carbonate, purified water, and coloring matter, and had a CT value of −136 HU, which is easily distinguished from other materials.

CT images were observed on the monitor, and three-dimensional images and animation images (four-dimensional images) thereof were submitted to observers for their decision.

As a result, it was proved that in the case of the existing products, the diffusion up to side sheets were large, thus resulting in a high probability of occurrence of the leakage.

The same experiment as above was performed except that the construction of the product was improved. As a result, it was proved that in the case of the improved product, the probability of the occurrence of leakage was remarkably low. As described above, it was understood that the present invention can be applied to not only the disposable diaper but also the sanitary napkin.

As shown in each Example, according to the method for displaying/analyzing a body fluid absorption mode of an absorbent article of the present invention, an improved product having, for example, a small leakage amount of drainage can be easily developed.

REFERENCE SIGNS LIST

1 X-ray CT apparatus
2 Disposable diaper
10 Driving means
20 Dummy doll
21 Artificial urine
31 Image processing means
32 Displaying means
34 Analyzing means

The invention claimed is:

1. A method for displaying/analyzing a body fluid absorption mode of an absorbent article comprising the steps of: in a state in which an absorbent article is put on a human body type dummy doll equipped with a body fluid-supplying means, photographing the absorbent article after the fluid is excreted from the dummy doll by an X-ray CT apparatus; and displaying/analyzing, based on the photographed image, the change with time of the absorption and diffusion state of the drainage into the absorbent article after the excretion in the state in which the absorbent article is put on the dummy doll, wherein:
the dummy doll is set on a bed which can move forward toward a photographing position of the X-ray CT apparatus;
after the bed is put into the photographing position, an X-ray source and a detector of the X-ray CT apparatus are turned around the dummy doll, while the body fluid-supplying means is driven to inject artificial urine into the dummy doll;
the artificial urine supplied by the body fluid-supplying means is passed through a path formed in the human body type dummy doll and drains from a private part of the dummy doll;
the change with time of the absorption and diffusion of the artificial urine in an absorbent article is measured by the X-ray CT apparatus; and
the absorbent article and the artificial urine is only displayed by using a window function of the X-ray CT apparatus.

2. The method for displaying/analyzing a body fluid absorption mode of an absorbent article according to claim 1, wherein the absorbent article is a disposable diaper having a CT value of −940 HU to −920 HU.

3. The method for displaying/analyzing a body fluid absorption mode of an absorbent article according to claim 1, wherein the X-ray CT apparatus has a helical scan photographing means and a multi-row detector of X-rays.

4. The method for displaying/analyzing a body fluid absorption mode of an absorbent article according to claim 1, wherein the photographed CT image is subjected to a reconstruction image processing to reconstruct a three-dimensional image, and the processed image is displayed on a displaying means.

5. The method for displaying/analyzing a body fluid absorption mode of an absorbent article according to claim 1, wherein the CT images of the drainage state with time are subjected to a reconstruction image processing to reconstruct a three-dimensional image, and the processed images changed with time are displayed as a moving image on a displaying means.

6. The method for displaying/analyzing a body fluid absorption mode of an absorbent article according to claim 1, wherein a body position of the human body type dummy doll equipped with the body fluid-supplying means is changed, and a change of an absorption mode of urine by the change of the body position is displayed/analyzed.

7. The method for displaying/analyzing a body fluid absorption mode according to claim 1, which comprises the steps of: previously knowing a relationship between a shape of a known dummy doll and a shape of a known absorbent article put on the doll; applying a shape of the absorbent article photographed to the dummy doll in the photographed image; understanding a relationship between the absorbent article and the photographed drainage; and understanding an absorption mode of the drainage in the absorbent article.

* * * * *